(12) United States Patent     (10) Patent No.: US 7,805,253 B2
Chen et al.     (45) Date of Patent: Sep. 28, 2010

(54) METHODS AND SYSTEMS FOR DISCOVERING PROTEIN MODIFICATIONS AND MUTATIONS

(75) Inventors: Xunming Chen, Bedford, MA (US); Philip J. Savickas, Franklin, MA (US); Marvin L. Vestal, Framingham, MA (US); Xiangping Zhu, Grafton, MA (US)

(73) Assignee: DH Technologies Development Pte. Ltd., Singapore (SG)

( * ) Notice: Subject to any disclaimer, the term of this patent is extended or adjusted under 35 U.S.C. 154(b) by 1339 days.

(21) Appl. No.: 11/217,257

(22) Filed: Aug. 31, 2005

(65) Prior Publication Data

US 2006/0110832 A1    May 25, 2006

Related U.S. Application Data

(60) Provisional application No. 60/606,405, filed on Aug. 31, 2004.

(51) Int. Cl.
*G01N 33/48* (2006.01)
*G01N 31/00* (2006.01)
*G06G 7/48* (2006.01)

(52) U.S. Cl. .............................. 702/19; 702/22; 703/11

(58) Field of Classification Search ....................... None
See application file for complete search history.

(56) References Cited

OTHER PUBLICATIONS

Peptide Sequencing via Tandem Mass Spectrometry, J. Comp. Bio. 6:3/4, 327-342, 1999.

*Primary Examiner*—Eric S Dejong
(74) *Attorney, Agent, or Firm*—John R. Kasha; Kasha Law LLC

(57) ABSTRACT

Accordingly, systems and methods for protein identification are provided. The present teaching provide for a system with one protein identification methodology based on one method and a second protein identification methodology based on a second protein identification methodology to interact and increase confidence in protein identification. Various embodiments employ protein identification methodologies that identify portions of a peptide. Various embodiments provide for a hypothesis generation module that can suggest modifications for the peptide based on differences between experimental and theoretical values. Various embodiments provide for an identifier module that can select one or more hypotheses from the hypothesis module as most probable. In this way, the present teachings can provide for systems and methods to combine protein identification results from multiple protein identification methodologies with the possibility of identifying modifications.

20 Claims, 6 Drawing Sheets

| | | |
|---|---|---|
| Beta Lactoglobulin | Cow | 500 |
| Cytochrome C | Horse | 500 |
| Catalase | Cow | 500 |
| G3P Dehydrogenase | Rabbit | 500 |
| Myoglobin | Horse | 500 |
| Conalbumin | Chicken | 500 |
| Lactoperoxidase | Cow | 500 |
| IGG | Pig | 500 |
| Glutathione S Transferase | Horse | 500 |
| Sero Transferrin | Cow | 50 |
| Lactate Dehydrogenase | Rabbit | 50 |
| Hemoglobin | Cow | 50 |
| Glutanic Dehydrogenase | Cow | 50 |
| Carboxypeptidase A | Cow | 50 |
| Bovine Serum Albumen | Cow | 50 |
| Alpha Amylase | Calcillus | 50 |
| Lysozyme C Precursor | Chicken | 50 |
| Carbonic Anhydrase | Cow | 50 |
| Phosphorylase B | Rabbit | 50 |
| Alpha Casein | | Calibrant |

FIG. 5

| Protein | Confirmation | Confidence(%) | Matcched Spectrums(>95% confidence) | Matched peptides |
|---|---|---|---|---|
| Beta Lactoglobulin | Confirmed | 100 | 8 | 8 |
| Cytochrome C | Confirmed | 100 | 23 | 19 |
| Catalase | Confirmed | 100 | 40 | 40 |
| G3P Dehydrogenase | From Pig | 100 | 17 | 15 |
| Myoglobin | Confirmed | 100 | 22 | 19 |
| Conalbumin | Confirmed | 100 | 20 | 26 |
| Lactoperoxidase | Confirmed | 100 | 30 | 32 |
| IGG | Confirmed | 100 | 4 | 9 |
| Glutathione S Transferase | From Human | 100 | 8 | 8 |
| Sero Transferrin | Confirmed | 100 | 14 | 21 |
| Lactate Dehydrogenase | Confirmed | 99.95 | 1 | 4 |
| Hemoglobin | Confirmed | 100 | 5 | 5 |
| Glutanic Dehydrogenase | Confirmed | 100 | 4 | 6 |
| Carboxypeptidase A | Confirmed | 100 | 1 | 1 |
| Bovine Serum Albumen | Confirmed | 100 | 11 | 18 |
| Alpha Amylase | Confirmed | 100 | 2 | 1 |
| Lysozyme C Precursor | Confirmed | 100 | 2 | 5 |
| Alpha Casein | Confirmed | 100 | 8 | 6 (Calibrant) |

METHODS AND SYSTEMS FOR DISCOVERING PROTEIN MODIFICATIONS AND MUTATIONS

CROSS-REFERENCE TO RELATED APPLICATIONS

This application claims priority from U.S. Provisional Application No. 60/606,405 filed on Aug. 31, 2004, which is incorporated herein by reference.

FIELD

The present teachings relate to methods and systems of identifying proteins and protein modifications via mass spectrometry. Cross-Reference to Related Applications

INTRODUCTION

Identification of peptides and proteins is often performed via mass spectrometry. Typically, an unknown protein is digested using a site-specific enzyme such as trypsin. The resulting peptides are ionized and passed into a first analyzer of a mass spectrometer. After selecting a precursor ion, the ion is fragmented and the intensities and the mass-to-charge ratios of the resulting fragment ions are measured by another mass analyzer. The result is commonly referred to as a MS/MS spectrum. This process can be repeated either collecting multiple spectra for the same precursor or collecting spectra for different precursors.

Peptide (precursor) identification often proceeds by in silico digesting a database of potential protein sequence matches using the cutting rules of the enzyme used for the experimental digestion. Then, the theoretical peptides with a mass-to-charge ratio (m/z) matching that of the precursor ion are theoretically fragmented to produce spectra. These theoretical spectra can be matched to the experimental spectra with the closest match indicating the most likely peptide. Generally the matches are scored via some scoring mechanism which is often referred to an ion score. If several peptides can be successfully identified and they belong to one protein, the protein may be reported as present. Typically a confidence value is reported along with the protein. Generally the more peptides that can be identified belonging to a protein, the higher the confidence in that protein being present.

Often only a small portion of MS/MS spectra can be matched to peptides, and thus contribute to the protein identification. Problems can occur when small differences from the normal protein state exist. These can be caused by a variety of circumstances including post-translational modification, the presence of single nucleotide polymorphisms, or a plurality of other factors. These modifications can cause a difference in the precursor mass of a peptide so that it does not correspond to the mass of the corresponding unmodified in silico peptide. This situation can preclude the proper peptide from consideration and can result in false weak matches for the peptide, or no match at all. This can happen despite the data quality being high. This in turn can decrease the confidence in subsequent protein identification. Also, in many instances, the goal of the research is to detect mutations and modifications. This can be the situations when looking for biomarkers and indicators of disease. Due to the mass mismatch, a modified peptide may be discarded from the analysis.

De novo protein sequencing coupled with MSBLAST provides another method for protein identification. This strategy can identify a protein based on partial peptide sequences. Even with unknown modifications, the de novo algorithm can generate a list of candidate peptide sequences from a MS/MS spectrum, most likely with part of the sequences being correct. MSBLAST can then find the closest sequence match between the de novo sequences and the protein sequences in a database. However, the de novo approach can have several problems. For example de novo sequencing very often can only yield small sequence tags. Another common type of error found in the sequence tags is same-mass segment replacement, i.e. a segment of amino acids is replaced with another one with the same mass. Current database search software such as MSBLAST generally cannot handle these sequence tag errors. As well, de novo sequencing algorithms usually cannot derive accurate sequences from low quality MS/MS spectra. De novo methods on their own may not be sufficiently robust and reliable when working with low quality data. The present teachings can provide a method to identify protein and peptide sequences and modifications to them.

BRIEF DESCRIPTION OF THE DRAWINGS

The skilled artisan will understand that the drawings, described below, are for illustration purposes only. The drawings are not intended to limit the scope of the present teachings in any way.

FIG. 5: A table showing a twenty protein mixture that is used in an example contained herein.

FIG. 6: A table listing the proteins identified by an embodiment of the present teachings in an example contained herein.

DESCRIPTION OF VARIOUS EMBODIMENTS

The section headings used herein are for organizational purposes only and are not to be construed as limiting the subject matter described in any way.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Computer Implementation

Figure 1:
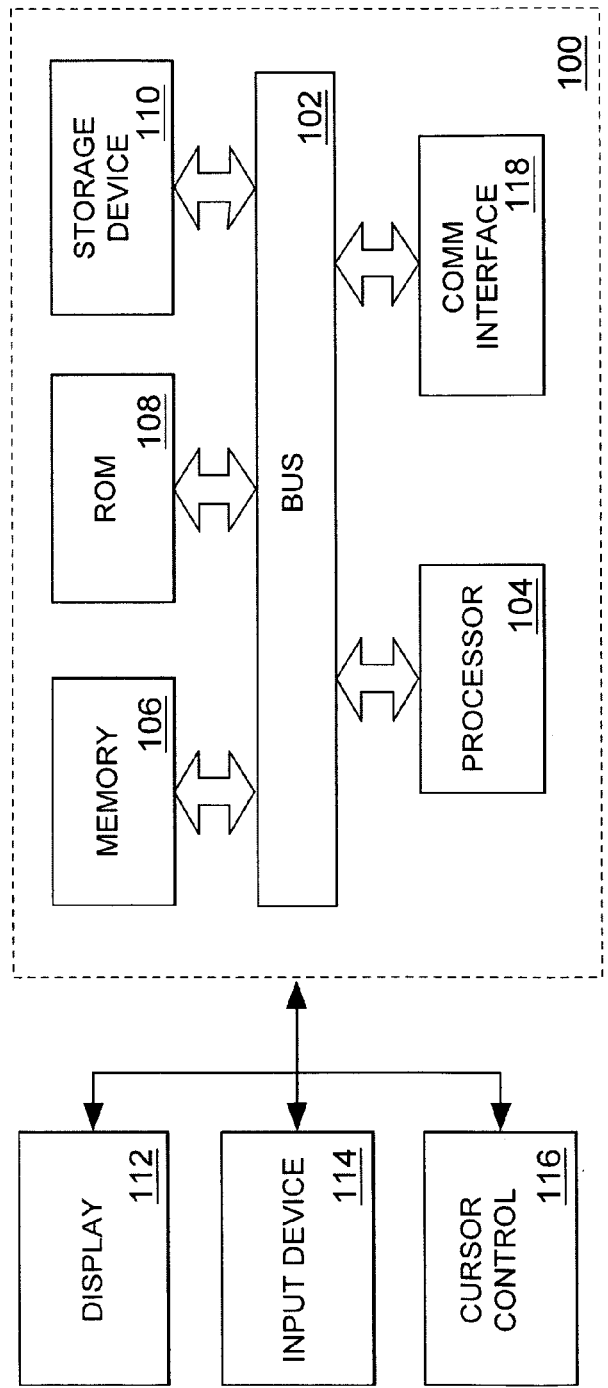
FIG. 1: Computer system on which embodiments of the present teachings can be realized.

FIG. 1 is a block diagram that illustrates a computer system 100, according to certain embodiments, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for identifying proteins, and instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (e.g., x) and a second axis (e.g., y), that allows the device to specify positions in a plane.

Consistent with certain embodiments of the present teachings, proteins can be identified by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process states described herein. Alternatively hard-wired circuitry may be used in place of or in combination with software instructions to implement the invention. Thus implementations of the present teachings are not limited to any specific combination of hardware circuitry and software.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102. Transmission media can also take the form of acoustic or light waves, such as those generated during radio-wave and infra-red data communications.

Common forms of computer-readable media include, for example, a floppy disk, a flexible disk, hard disk, magnetic tape, or any other magnetic medium, a CD-ROM, any other optical medium, punch cards, papertape, any other physical medium with patterns of holes, a RAM, PROM, and EPROM, a FLASH-EPROM, any other memory chip or cartridge, a carrier wave, or any other medium from which a computer can read.

Various forms of computer readable media may be involved in carrying one or more sequences of one or more instructions to processor 104 for execution. For example, the instructions may initially be carried on magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

Protein and Modification Identification

Figure 2:
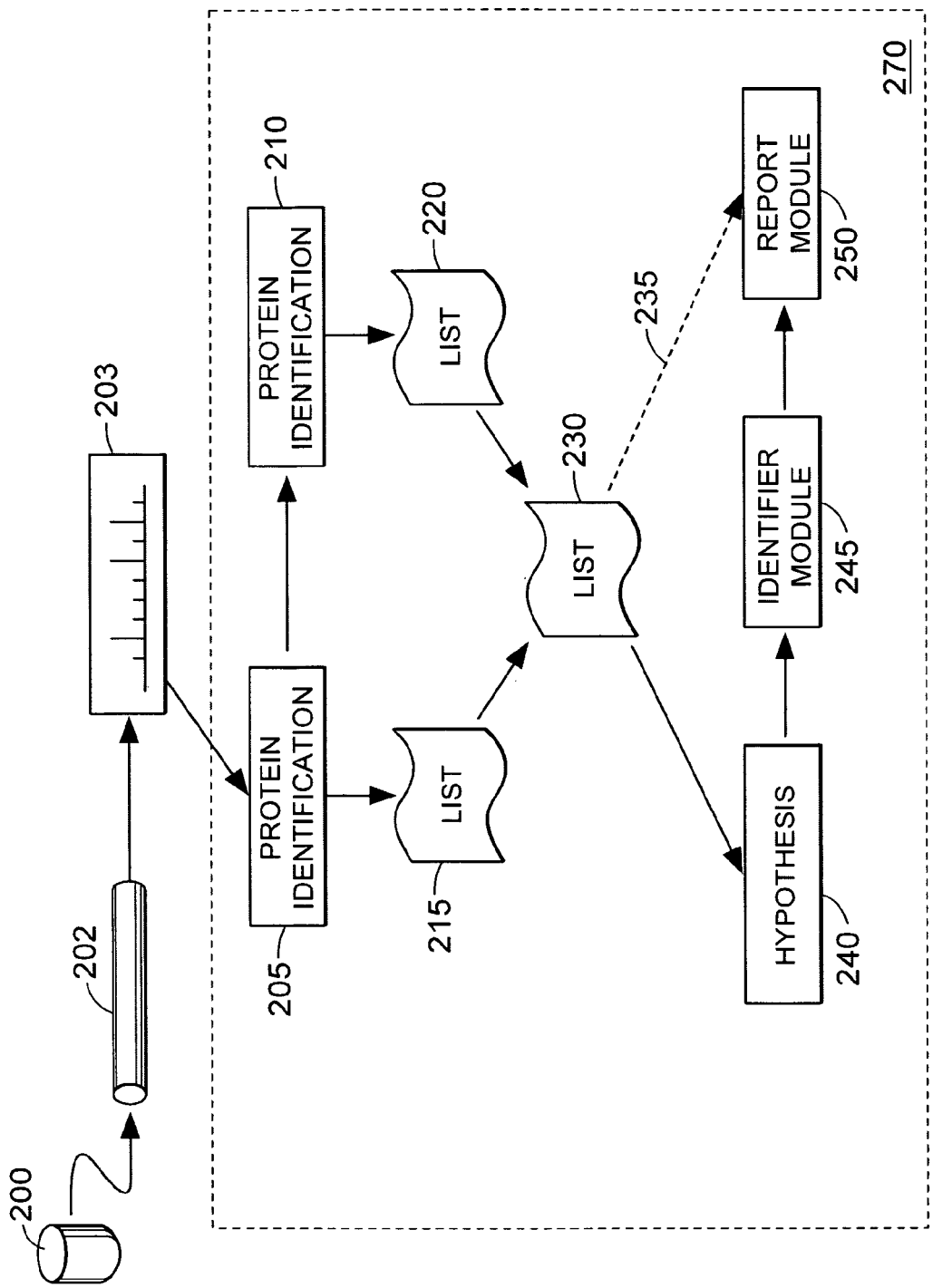
FIG. 2: An embodiment of the present teachings which can be used to identify proteins and protein modifications. Information from two protein identification methods are used to confirm the presence of the protein and identify modifications.

FIG. 2 illustrates an embodiment of the present teachings that can be used to perform protein identification. Sample 200 is analyzed by mass spectrometer 201 to produce mass spectrometry data 202. The present teachings are generally not specific to a particular type of mass spectrometer. For example, mass spectrometers employing different ionization techniques such as electrospray ionization or matrix-assisted laser desorption ionization (MALDI) or a variety of other techniques can be used. Similarly, mass spectrometers using a variety of analyzers can be used. For example the present teachings can be used with data from instruments employing analyzers based on quadrupoles, ion traps, time-of-flight measurement devices, as well as analyzers based on other principles. The output of a mass spectrometer 202 is typically a spectrum 203 which is often reduced to a peak list where peaks are identified by intensity and mass-to-charge ratios. Generally a peak can be associated with a peptide or peptide fragment. In the case of an MS scan, the peaks are usually associated with peptides that result from enzymatic digestion. In the case of an MS/MS scan, one of the digest peptides is usually fragmented and the peak list reflects information about the plurality of sub fragments that can be formed from the selected peptide. One skilled in the art will understand these general concepts.

System 270 can be used to identify the protein or proteins that the selected peptide originated from. Using a first protein identification method 205 the mass spectrometer data can be used to identify individual peptides. One method commonly employed compares the peak list from the mass spectrometer data to a peak list generated by computationally digesting a database of proteins using the same cutting rules as the enzyme used in the experiment, and then fragmenting the resulting peptides along the peptide backbone. A variety of scoring mechanisms can be employed to assign a mass spectrum a match score. This score can be used to determine which matches can reliably be used to identify the proteins from which they originated. The evidence for a particular protein can be aggregated and if enough evidence is present, that protein is declared as present in the sample. Method 205 will generally output a list of proteins 215 that may be present in sample. Often times, but not necessarily, a protein confidence value or quality value is also output with the proteins. This value can indicate the degree of confidence in the protein identification.

It can be the case that not all mass spectra are reliably identified by 205. System 270 can pass unmatched mass spectra and or weakly matched by method 205 to a second protein identification method 210. Weak matchings can be defined by allowing the user to set a threshold for the mass spectrum match score. Various embodiments employ a de novo sequencing identification technique for method 210. This technique can be useful when a spectrum cannot be matched with a high degree of certainty to a peptide from the database. This can occur in a variety of situations. A common cause of mismatches is the presence of one or more post-translational modifications. De novo peptide sequencing can be performed by calculating the mass differences between ion peaks. Delta masses matching known masses of single (or double) amino acid residues are noted, and attempts are made to extend the residue sequence in an iterative manner. Putative sequences can be ranked using a score incorporating factors such as unbroken peak series. A variety of different algorithms exists and one skilled in the art will be able to make use of the variety of references available on the subject. One such reference is *De Novo Peptide Sequencing via Tandem Mass Spectrometry*, J. Comp. Bio. 6:3/4, 327-342, 1999.

In some cases, the de novo technique will only be able to reliably identify short sequence tags that appear in the peptide. In such cases, the tags can be matched to proteins contained in a database or to the theoretical peptides that result from their digestion as mentioned in the spectrum-matching technique discussed earlier with reference to method 205. Matching can be preformed via a variety of alignment tools such as BLAST-type algorithms. These techniques can be used to identify peptides that have a significant proportion of their sequence explained by the de novo generated sequence information. The output of method 210 is typically a list 220 of proteins that might be present in the sample. Confidence values may accompany these proteins.

If a spectrum did not match any peptide sequence during database searching, using method 205, but led to the confident identification of a known protein using a de novo/MSBLAST, a possible explanation is that the corresponding peptide has an unknown modification/mutation. If a protein appears in both lists 215 and 220, there is a greater likelihood that it is present, this can be the case even if the confidence of the protein in each list is fairly low because the combination of protein ID tools based on different protein identification methods were able to identify the protein independently using potentially different sets of data. The present teachings provide for systems predicated on two or more different identification methods that can help pinpoint the location of unknown modifications/mutations, as well as aid in the identification of proteins.

Figure 3:
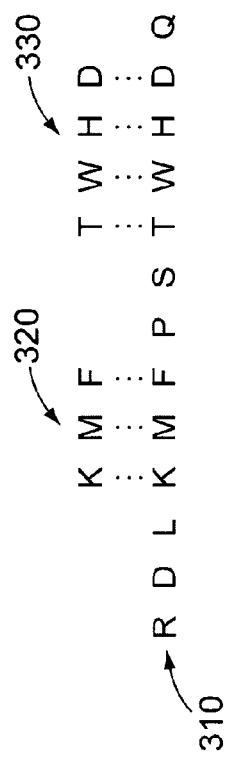
FIG. 3: An example demonstrating the alignment of sequence tags identified by de novo sequencing. The sequence tags KMF and TWHD were identified by de novo sequencing from a possibly poor quality spectrum. The tags are aligned to the sequence RDLKMFPSTWHDQ. Potential sites for modification include R,D,L,P,S,Q and the C-, and N-termini.

After protein identification via a protein identification module 205 some of the proteins in the sample will be identified and their sequences can be retrieved. A temporary database with the identified protein and sequences can be created. The unmatched or weakly matched spectra can then be submitted to protein identification module 210. This may identify some of the same proteins as in the temporary protein database and a list of intersecting proteins via a list comparison module at 230 can be generated. In the case of method 210 being a technique that provides a partial match to peptides such as a de novo/MSBLAST approach, the match is likely partial due to unknown modifications/mutations. Additional modules can be employed to help identify modifications. This can be employed by retrieving the full spectrum for the peptide corresponding to the one or more sequence tags and overlaying the tags on the sequence. This process is illustrated in FIG. 3. Here, the full peptide sequence RDLKMFPST-WHDQ is illustrated at 310. In this example, two peptide tags KMF 320 and TWHD 330 were identified during method 210 processing. The amino acids that are unmatched can be result from several factors. They could be due to the fact that the data was of sufficiently poor quality that the sequence tag could not be expanded reliably or, they might be sites of modifications.

In various embodiments, module 230 can generate modifications hypotheses about the state of the remaining amino acids. For example, the sequence 310 has a mass of 1641 Daltons. If the mass of the precursor that yielded tags 320 and 330 was 1641 Daltons, then it is likely that the unmatched amino acids are the same as the amino acids contained in the reference peptide. If the precursor mass and the mass of the reference sequence do not match, hypothesis module 240 can calculate the difference between the two sequences and propose modifications, such as post-translational modifications, insertions, deletions etc. The hypothesis module can determine likely modifications by consulting data stored internally about typical modifications and the mass changes that they entail. One skilled in the art will appreciate that such information is available from sources such as http://www.expasy.org/tools/findmod/findmod_masses.html, and http://www.abrf.org/index.cfm/dm.home. The hypothesis module can store this information and be updated as new modifications are discovered. The module can propose modifications based on single modifications or multiple modifications that when taken together can explain the mass difference. For example, in the case of single modifications a modification corresponding to the mass difference can be applied to each unmatched amino acid where it might appear, and a score is calculated as a measure of the fit between the observed MS/MS spectrum and the putative peptide sequence. In the case of multiple modifications, two or more modifications whose sum is close to the mass difference can be proposed as a hypothesis and fitted to the unmatched amino acids.

An identifier module 245, can rank the proposed modifications based on a score that reflects the modifications ability to explain the mass difference. The identification module can also take into account additional factors such as the frequency of such modifications occurring. These frequencies can be stored with the modifications and can be user modified. The ability to modify the frequencies can be useful in situations where the scientist has purposefully subjected the sample to a reaction intended to produce certain modifications.

Figure 4:
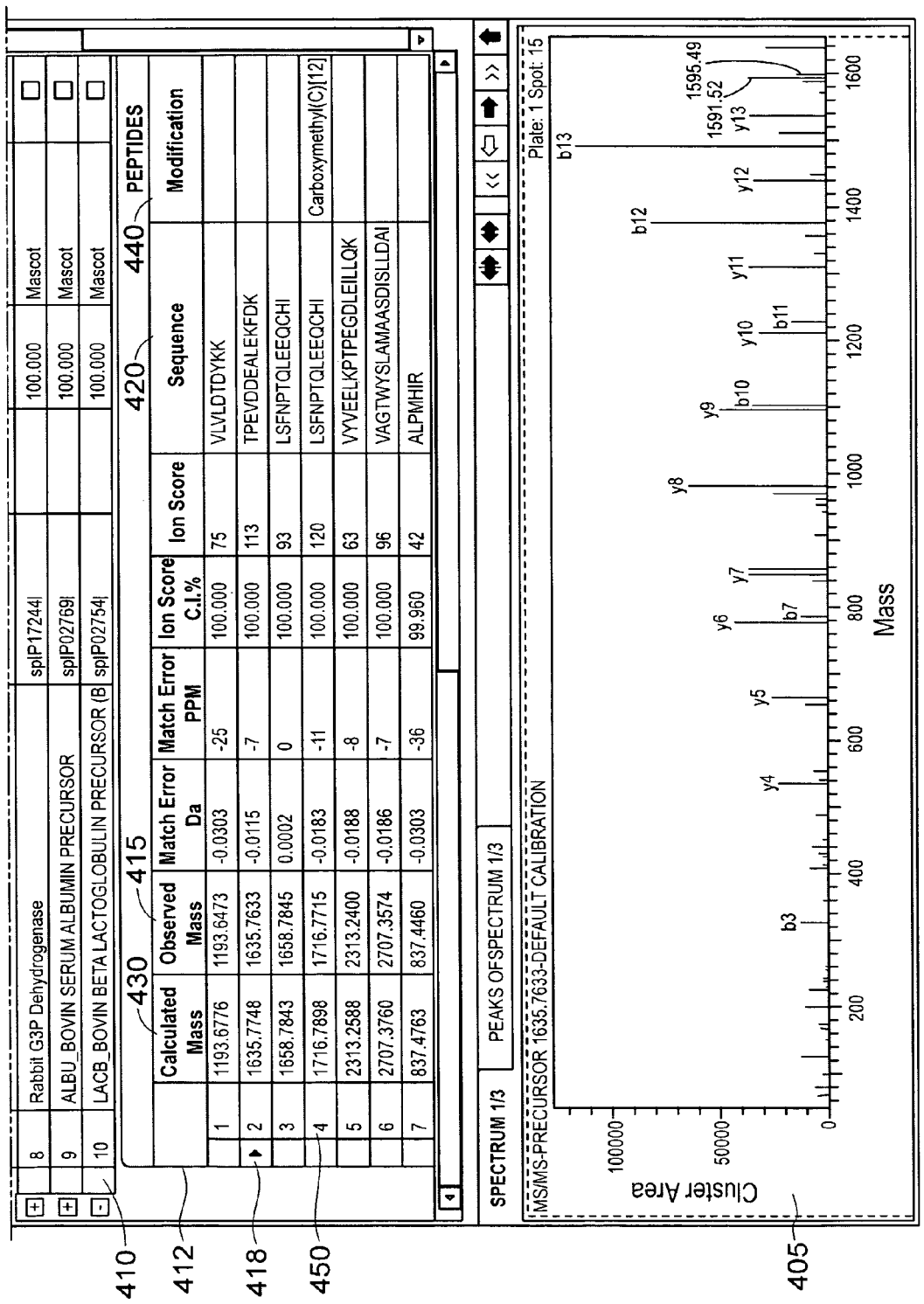
FIG. 4: An embodiment of the present teachings illustrating a possible way to report results to the user. The protein Beta Lactoglobulin was identified by multiple MS/MS spectra from several peptides. The peptide LSFNPTQLEEQCHI contained the Carboxymethyl modification. Inclusion of the mass of this modification leads to a calculated precursor mass that matches the observed precursor mass thus leading to a positive identification of the peptide and the modification.

A report module 250 can output the results to the user. FIG. 4 illustrates an embodiment of the present teachings as implemented on a computer graphical device. Post analysis, the identified protein is reported at row 410 using a display mechanism that permits the underlying evidence supporting that protein to be either hidden from view or shown on the device. Table 412 contains the peptide information supporting the presence of the protein. Column 420 gives the sequence of the identified peptide. Column 415 gives the mass of the precursor. Since row 2 is selected at 418 the experimental spectrum associated with that peptide is shown in the panel below 405. The spectrum at 405 has a precursor mass of 1635.7633 Daltons which corresponds to the mass calculated by adding the masses of the amino acids of the sequence contained in corresponding column 420. The calculated mass is displayed in column 430. Row 450 shows an identified sequence that results in a calculated mass that is initially not the same as the observed mass. The calculated mass for the sequence LSFNPTQLEEQCHI is 1658.8528. When subtracted from the precursor mass leaves a mass of 57.937 Daltons unaccounted for. This difference can be computed in the hypothesis module 240 which can then use stored information to determine that adding a Carboxymethyl modification to the Cysteine amino acid would result in an addition of 58 Daltons to the peptide. Other modifications might be possible and the identification module at 245 can determine that the Carboxymethyl modification results in a calculated mass of 1716.7898 which is close to the precursor mass. Thus the sequence is reported and the modification leading to the positive identification is shown in column 440.

The factoring of functionalities as depicted in FIG. 2 is not intended to limit the present teachings in any way. One skilled in the art will appreciate that several of the modules can be contained in one module. For example, the hypothesis and identifier modules can be implemented as one module. As well, not all modules need be present for some embodiments of the present teachings to operate correctly. For example, if the goal is only enhanced protein identification without concern for modification identification, the hypothesis modules and identification modules may not be present and information may flow as depicted by the broken arrow 235.

The present teachings can be integrated with instrument data collection workflows. One such example is the Results Dependent Analysis workflow from Applied Biosystems that is described in US patent application US2003000646371 filed on Aug. 22, 2003. Incorporation of the present teachings may reduce the number of spectra required for protein identification. Such a combined workflow can be used to achieve both high throughput protein identifications and modification discovery and can be useful in complex data regimes. For example, such a workflow can be used in liquid chromatography MS/MS systems where several proteins are digested together and subsequently analyzed based on their elution time.

Examples

Aspects of the present teachings may be further understood in light of the following examples, which should not be construed as limiting the scope of the present teachings in any way.

A twenty-protein mixture was digested, separated by liquid chromatography and spotted onto a MALDI plate. The proteins contained in this mixture are listed in FIG. 5. The first column lists the protein, the second column lists the species that the protein came from and the third column gives the concentration on the protein in femtomoles.

A total of 613 MS-MS spectra were collected from the plate and submitted to protein identification method 205. The method employed in 205 is the spectrum-matching technique described herein. Of the 613 spectra, only 234 MS/MS spectra matched peptides with a confidence greater than ninety-five percent. The spectra however did lead to high-confidence, correct identification of eighteen proteins. These proteins are listed in FIG. 6. In FIG. 6, columns three through 5 give the confidence associated with the protein identification, the number of matched spectra with a confidence greater than ninety-five percent and the number of matched peptides in the protein. The 379 spectra not contributing to the protein identification either matched to a peptide with a very low score or were not matched at all, even though most of the spectra were of high quality.

Figures 7, 8:
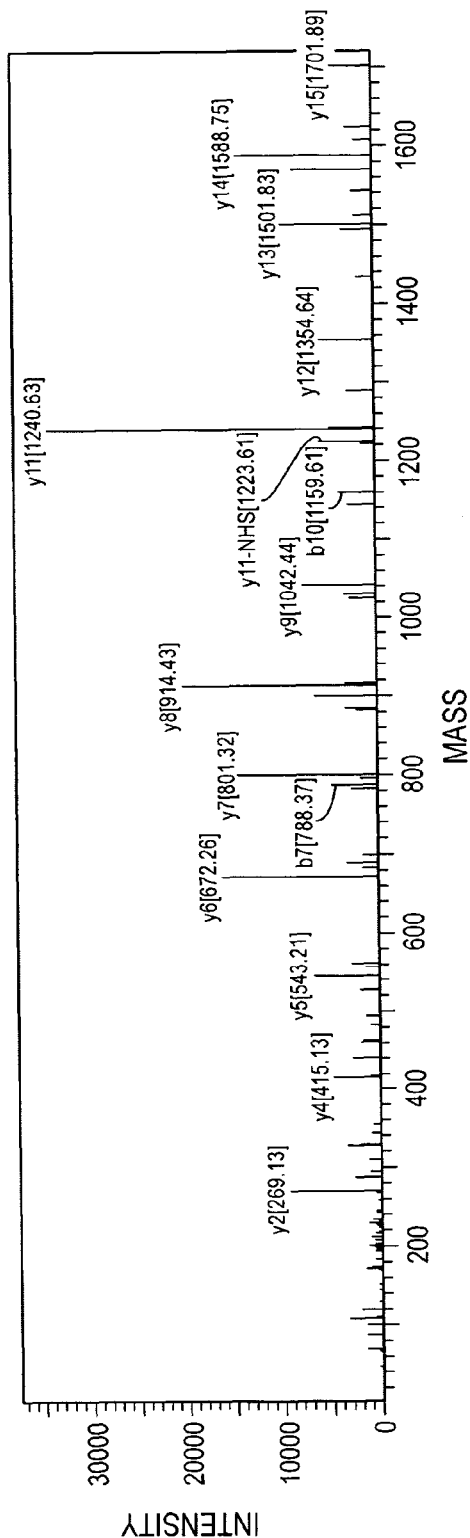
FIG. 7: Illustrates the spectrum of a peptide with a precursor mass of 1701.7853 Daltons. An unknown modification is discovered via an embodiment of the teachings herein.
FIG. 8: A table listing modifications identified on peptides associated with the twenty protein mixture used as an example herein.

From the unmatched MS/MS spectra, twenty were submitted to a second protein identification method 210. The method employed in 210 is the de novo/MSBLAST method described herein. One of the unmatched spectra is shown in FIG. 7. This figure shows a high-quality spectrum for a peptide with a mass of 1701.7853. This MS/MS spectrum did not match any peptides identified by the first protein identification method 205 but did result in the identification of a protein that was also identified by method 205. De novo partial sequencing of the spectrum in FIG. 7 resulted in the sequence LSFNPT-KLEEK which was MSBLAST matched to the peptide LSFNPTQLEEQ found in Beta Lactoglobulin. This protein is one of the proteins identified by method 205. The full peptide sequence found in this protein is LSFNPTQLEEQCHI which has a mass of 1658.8528 Daltons. Hypothesis module 240 hypothesized that modifying the Cysteine by 43 Daltons results in an overall peptide mass close to the mass of the precursor and thus a high score was assigned to the modification. The residue mass of Cysteine plus 43 Daltons does not match the mass of any known amino acid. Thus the delta mass is likely caused by a modification, not a mutation. Identifier module 245 chose the Cysteine modification as correct. Examination of a table of known modifications shows that the modification is probably the Carbamyl modification.

Of the twenty unmatched spectra submitted to 210 six spectra were identified by protein identification method 210. These spectra identified modifications that might have otherwise gone undiscovered without the present teachings. Modifications identified are show in FIG. 8. Column one contains the mass of the precursor. Column three shows the de novo partial sequence identified while column four shows the sequence it was matched to. Column two identifies the protein, while column five gives the full peptide sequence. The underlined portions of the peptide sequences give the amino acids not identified by de novo sequencing. These are sites of potential modifications. The final column, column six gives modification that resulted in a precursor mass match when added to the mass of the sequence contained in column five.

The foregoing description has been presented for purposes of illustration and description. It is not exhaustive and does not limit the invention to the precise form disclosed. Modifications and variations are possible in light of the above teachings or may be acquired from practice. Additionally, the described implementation includes software but the present teachings may be implemented as a combination of hardware and software or in hardware alone. The present teachings may be implemented with both object-oriented and non-object-oriented programming systems.

The invention claimed is:

1. A system for identifying proteins and modifications from two or more identification methods, comprising:
    a mass spectrometer that measures a plurality of spectra from a sample; and
    a processor in communication with the mass spectrometer that
        receives the plurality of spectra from the mass spectrometer and produces a plurality of peak lists from the plurality of spectra,
        performs a first identification method that compares a first peak list from the plurality of peak lists with a peak list generated by computationally digesting a first protein database producing a first list of proteins from the comparison,
        performs a second identification method that applies a de novo peptide sequencing technique to a second peak list from the plurality of peak lists producing one or more putative sequences and matches the one or more putative sequences to a second protein database using an alignment tool producing a second list of proteins from the matching,
        if a protein of the second list of proteins matches a protein of the first list of proteins, performs a first comparison of the precursor peptide of the second peak list to a full peptide sequence found in the protein, if the precursor peptide does not match the full peptide sequence in the first comparison, performs a second comparison of a difference between the precursor peptide and the full peptide sequence to a modification database, and if a modification from the modification database that matches the difference is found from the second comparison, identifies the protein in the sample from the precursor peptide and the modification.

2. The system of claim 1, wherein the processor performs the second identification method on the second peak list if the processor performs the first identification method on the second peak list and no matched proteins are produced.

3. The system of claim 1, wherein the processor performs the second identification method on the second peak list if the processor performs the first identification method on the second peak list and only weakly matched proteins are produced.

4. The system of claim 1, wherein the first list of proteins includes a protein confidence value that indicates the degree of confidence in the protein identification.

5. The system of claim 1, wherein the difference between the precursor peptide and the full peptide sequence comprises a mass difference.

6. The system of claim 5, wherein the processor ranks the modification based on a score that reflects the ability of the modification to explain the mass difference.

7. The system of claim 1, wherein the processor ranks the modification based on a frequency of such a modification occurring.

8. A method for identifying proteins and modifications from two or more identification methods, comprising:
    measuring a plurality of spectra from a sample using a mass spectrometer;
    receiving the plurality of spectra from the mass spectrometer and producing a plurality of peak lists from the plurality of spectra using a processor;
    performing a first identification method that compares a first peak list from the plurality of peak lists with a peak list generated by computationally digesting a first protein database producing a first list of proteins from the comparison using the processor;
    performing a second identification method that applies a de novo peptide sequencing technique to a second peak list from the plurality of peak lists producing one or more putative sequences and matching the one or more putative sequences to a second protein database using an alignment tool producing a second list of proteins from the matching using the processor;
    if a protein of the second list of proteins matches a protein of the first list of proteins, performing a first comparison of the precursor peptide of the second peak list to a full peptide sequence found in the protein using the processor,
    if the precursor peptide does not match the full peptide sequence in the first comparison, performing a second comparison of a difference between the precursor peptide and the full peptide sequence to a modification database using the processor, and
    if a modification from the modification database that matches the difference is found from the second comparison, identifying the protein in the sample from the precursor peptide and the modification using the processor.

9. The method of claim 8, further comprising performing the first identification method on the second peak list, and if no matched proteins are produced, performing the second identification method on the second peak list.

10. The method of claim 8, further comprising performing the first identification method on the second peak list, and if only weakly matched proteins are produced, performing the second identification method on the second peak list.

11. The method of claim 8, wherein the first list of proteins includes a protein confidence value that indicates the degree of confidence in the protein identification.

12. The method of claim 8, wherein the difference between the precursor peptide and the full peptide sequence comprises a mass difference.

13. The method of claim 12, further comprising ranking the modification based on a score that reflects the ability of the modification to explain the mass difference using the processor.

14. The method of claim 8, further comprising ranking the modification based on a frequency of such a modification occurring.

15. A computer program product, comprising a computer-readable storage medium whose contents include a program with instructions being executed on a processor so as to perform a method for identifying proteins and modifications from two or more identification methods, the method comprising:
    providing a system, wherein the system comprises distinct software modules, and wherein the distinct software modules comprise a measurement module, a first identification modules, a second identification module, a comparison module, a hypothesis module, and an identifier module;
    receiving a plurality of spectra from a mass spectrometer that measured the plurality of spectra from a sample using the measurement module;
    producing a plurality of peak lists from the plurality of spectra using the measurement module;
    performing a first identification method that compares a first peak list from the plurality of peak lists with a peak list generated by computationally digesting a first protein database producing a first list of proteins from the comparison using the first identification module;
    performing a second identification method that applies a de novo peptide sequencing technique to a second peak list from the plurality of peak lists producing one or more putative sequences and matching the one or more putative sequences to a second protein database using an alignment tool producing a second list of proteins from the matching using the second identification module;
    if a protein of the second list of proteins matches a protein of the first list of proteins, performing a first comparison of the precursor peptide of the second peak list to a full peptide sequence found in the protein using the processor using the comparison module,
    if the precursor peptide does not match the full peptide sequence in the first comparison, performing a second comparison of a difference between the precursor peptide and the full peptide sequence to a modification database using the hypothesis module, and
    if a modification from the modification database that matches the difference is found from the second comparison, identifying the protein in the sample from the precursor peptide and the modification using the identifier module.

16. The computer program product of claim 15, further comprising performing the first identification method on the second peak list, and if no matched proteins are produced, performing the second identification method on the second peak list.

17. The computer program product of claim 15, further comprising performing the first identification method on the second peak list, and if only weakly matched proteins are produced, performing the second identification method on the second peak list.

18. The computer program product of claim 15, wherein the first list of proteins includes a protein confidence value that indicates the degree of confidence in the protein identification.

19. The computer program product of claim 15, wherein the difference between the precursor peptide and the full peptide sequence comprises a mass difference.

20. The computer program product of claim 19, further comprising ranking the modification based on a score that reflects the ability of the modification to explain the mass difference using the identifier module processor.

* * * * *